(12) United States Patent
Cardona Burrul

(10) Patent No.: US 7,291,115 B2
(45) Date of Patent: Nov. 6, 2007

(54) SPIROMETER AND METHOD TO MEASURE THE VENTILATORY FUNCTION BY SPIROMETRY

(75) Inventor: Francisco Cardona Burrul, Barcelona (ES)

(73) Assignee: Health Solutions, S.L., Barcelona (ES)

( * ) Notice: Subject to any disclaimer, the term of this patent is extended or adjusted under 35 U.S.C. 154(b) by 315 days.

(21) Appl. No.: 10/494,443

(22) PCT Filed: Nov. 5, 2001

(86) PCT No.: PCT/ES01/00422

§ 371 (c)(1),
(2), (4) Date: May 4, 2004

(87) PCT Pub. No.: WO03/053243

PCT Pub. Date: Jul. 3, 2003

(65) Prior Publication Data

US 2004/0260195 A1 Dec. 23, 2004

(51) Int. Cl.
*A61B 5/08* (2006.01)
(52) U.S. Cl. ...................... 600/538; 600/529
(58) Field of Classification Search ......... 600/529–543
See application file for complete search history.

(56) References Cited

U.S. PATENT DOCUMENTS

| | | | | |
|---|---|---|---|---|
| 3,606,883 A | * | 9/1971 | Lux | 600/538 |
| 3,735,752 A | * | 5/1973 | Rodder | 600/537 |
| 3,949,737 A | * | 4/1976 | Nielsen | 600/539 |
| 4,034,743 A | * | 7/1977 | Greenwood et al. | 600/538 |
| 5,158,094 A | * | 10/1992 | Miller | 600/539 |
| 5,816,246 A | | 10/1998 | Mirza | 128/726 |
| 5,924,994 A | | 7/1999 | Harbrecht et al. | 600/532 |
| 6,648,820 B1 | * | 11/2003 | Sarel | 600/300 |

FOREIGN PATENT DOCUMENTS

WO  9718753  5/1997

* cited by examiner

*Primary Examiner*—Charles A. Marmor, II
*Assistant Examiner*—Karen E Toth
(74) *Attorney, Agent, or Firm*—Wolf Block Schorr & Solis-Cohen LLP

(57) ABSTRACT

The function of the multispirometer and procedure to measure the ventilatory function by spirometry is to know how a person exhales or expels air with the objective to study and monitor the functioning of his/her lungs and many pathologies. By means of this method, the ventilatory function by spirometry is measured, and is capable of obtaining respiratory restriction and obstruction values of a patient. To perform the above mentioned method, an electronic spirometer provided with flow detector means, microprocessor control means to carry out calculations on the basis of measured data, and means associated to said microprocessor to store the measured results, to visualize the results and to compare the stored results, is used.

18 Claims, 2 Drawing Sheets

SPIROMETER AND METHOD TO MEASURE THE VENTILATORY FUNCTION BY SPIROMETRY

The present invention, a spirometer and method to measure the ventilatory function by spirometry has the function to know how a person exhales or expels air with the objective to study and monitor the functioning of his/her lungs and many pathologies.

Spirometry is the measurement of volumes and flows of expired air—and sometimes inspired air—for the purpose of determining pulmonary ventilatory function. The spirometer is the device that carries out this function.

The main ventilatory function parameters are:

VC—Vital Capacity, which is the maximal volume of air exhaled from a point of maximal inhalation or the air inhaled from a point of maximal exhalation. It can be measured by inhalation, forced exhalation or slow exhalation, being preferable to choose the highest value of them all. The VC is expressed in liters and in percentage of the patient's theoretical/reference value. It becomes altered in heart failure and diseases of the lung and thorax.

FVC—Forced Vital Capacity, which is the maximal volume of air exhaled with maximal effort from a position of maximal inhalation. It is expressed in liters and in percentage of a patient's reference value.

FEV1, which is the maximum volume of air exhaled during the first second of maximum effort from a maximum inhalation. It is expressed in liters and in percentage of the patient's reference value. It becomes altered in cases of bronchial obstruction and it is fundamental for diagnosing and monitoring asthma and obstructive diseases.

PEF—Peak Expiratory Flow, which is the highest expiratory flow achieved with maximal effort from a position of maximal inspiration. It is expressed in liters/second or in liters/minute.

BACKGROUND OF THE INVENTION

The current state of the art includes four different types of simple measuring devices and spirometers:

Peak flow or maximum flow measuring devices, that do not measure the ventilatory function; their use is limited to home monitoring of this parameter for a single patient for asthma but not for any other respiratory diseases.

Peak flow electronic measuring devices, with or without FEV1 measurement (Forced Expiratory Volume in the first second). These devices do not measure the ventilatory function and their use is the same as simple measuring devices with the advantage that they are more precise but not very accurate, and that they also can store and calculate variability. The ATS (American Thoracic Society) recommends a PEF (peak expiratory flow) maneuver for peak flow monitoring different from the conventional FVC maneuver, from which the FEV1 is obtained. This PEF maneuver consists of a sharp and sudden forced exhalation from a position of maximal inspiration reaching maximum flow normally in one tenth of a second, depending on the effort and volume, and not allowing the FEV1 to be obtained.

The above-mentioned measuring devices—in spite of being affordable—do not allow screening, spirometric diagnosis, follow-up of ventilatory disorders or valuation of variability or functional situation in pathologies different from asthma, as in the case of chronic obstructive pulmonary diseases.

Other presently available spirometers are:

Monitoring spirometers to measure the ventilatory function; they are portable and allow a trained patient to evaluate and monitor their ventilatory function by means of FVC maneuvers, and some also use inspiratory maneuvers. These spirometers, in spite of their reduced size and handling, have not been designed to adapt to the various clinical situations where it is necessary to measure ventilatory functions such as the case in pharmacies, emergency rooms, hospitals or clinics, use by subjects that are untrained or with little ability, or subjects suffering from coughing, dyspnea, and/or intense bronchial obstruction Laboratory spirometers designed to measure the ventilatory function and to carry out studies in Centers by qualified personnel. A great disadvantage of these spirometers is their high cost and the requirement for calibration and disinfection systems that make them only accessible to certain professionals, specialized centers and hospitals. With these devices it is not possible to measure the various types of functional variability as they do not allow monitoring and therefore they cannot be used for diagnosing the type of asthma and/or chronic bronchitis that the patient presents with nor the response to treatment.

Simple measuring devices for respiratory parameters such as peak flow and FEV1 do not measure the ventilatory function in spite of being more affordable than monitoring and laboratory spirometers. Although the latter do measure ventilatory function they do not adapt themselves to the various clinical situations where the determination of this function is necessary.

Spanish patent, ES2073542, requested by GLAXO AUSTRALIA PTY., LTD. describes an electronic measuring device that only measures two parameters: the volume expired in one second in liters, and the expiratory peak flow rate. With these parameters it is not possible to completely and accurately determine the ventilatory function.

French patent FR2729072 requested by FRANCOIS JEAN, also describes a measuring device similar to the previously described one, and measuring the same parameters. This device can be used in several medical applications; however, it provides no option to customize different clinical situations.

Application PCT, WO97/18753, requested by TIUS ELCON LTD., describes a measuring device similar to the aforementioned ones for home monitoring of asthma; its main application is monitoring the response to the patient's medication. This device calculates the best value measured over a period of time, several days of measurements, determined by the patient himself as a base, without the assistance of an expert. This does not provide a reliable baseline result to be compared with subsequent measurements.

As indicated above, the ventilatory function cannot be measured at present in most situations where this is required, contrary to the case for determining the blood glucose level and blood pressure. For this reason and according to all studies published, respiratory conditions such as asthma or chronic obstructive pulmonary disease—which are as or more frequent than diabetes or arterial hypertension—are not detected early, are not properly diagnosed, are underestimated and are treated incorrectly, thus resulting in high morbidity, mortality and health care costs that could be avoided.

VC and FEV1 are two excellent health markers, as important as, or even more than, blood pressure, glucose, cholesterol or weight; however, nobody knows their VC or FEV1 or what these values mean.

The multispirometer and the method to measure ventilatory function by spirometry as described below, overcomes the problems posed by existing measuring devices and spirometers.

BRIEF SUMMARY OF THE INVENTION

The pulmonary ventilatory function involves the process of inhaling and exhaling air from the lungs. By knowing how air is inhaled and, most importantly, how air is exhaled, much may be known about the functioning of the lungs and their pathologies.

The method to measure ventilatory function by spirometry can be used by an electronic spirometer with flow detection means, such as the turbine type.

A spirometer can perform varied types of measurements; however, the two most basic and required measurements are:

Vital capacity (VC) is the maximum quantity or maximum air volume in liters that a patient is capable of exhaling after having inspired all the air possible and having expelled it completely.

The forced expiratory volume in the first second (FEV1) (we shall call it FEV) represents the maximum quantity or maximum air volume in liters that a subject is capable of exhaling during the first second after having inspired all air possible and having expelled it with a maximally forced and continuous effort.

With the above two parameters the spirometer can obtain the ventilatory function of the patient, such as:

Normal ventilatory function, which means that the subject has a VC and FEV within the reference values corresponding to his/her age, height, weight and ethnic group, that is, ventilation or "respiration" and a bronchial caliber considered to be normal.

Obstruction and its intensity, which means that the subject's bronchi or respiratory conduits are obstructed or closed preventing proper passage of the air. This obstruction is detected when the FEV/VC ratio is reduced; this could be due to some obstructive bronchial disease such as asthma or chronic bronchitis. The intensity of the obstruction is determined by a reduced FEV Restriction and its intensity, which means that a subject can expel less quantity of air than normal without presenting with an obstruction. This restriction is detected when VC is reduced and the FEV/VC ratio is normal; this could be due to several diseases of the lung and thoracic cavity, heart failure, and/or significant excess weight.

Reduced Vital Capacity (VC) and obstruction, that could be due to the same obstruction that does not let the patient expel all the air required and/or due to another associated lung or heart pathology.

The multispirometer and the method to measure the ventilatory function by spirometry, object of this patent application, bring the measure of the ventilatory function at the reach of any user, have multiple applications and are easily adaptable to different clinical situations. The following are some of the applications and clinical situations where the spirometer and the method are applicable: study on persons that are not sufficiently skilled to carry out maneuvers (i.e. children and the elderly); study on people with heavy cough, dyspnea and/or bronchial obstruction; pharmacies; medical services, such as emergency rooms, clinics and hospitals, health centers, ambulatory clinics, doctors and nurses; home, work and/or effort monitoring; medical check-ups; nursing homes; schools; work and sports medicine; indefinite self-monitoring; home assistance and Call-Center monitoring.

In order to achieve this, the method is based principally on a novel procedure as per the following steps which are described below:

Simple test option with VC (slow) maneuver and FEV maneuver, and full test option with VC maneuver and FVC maneuver.

FEV maneuver index (IM). Personal maneuver index (IMP).

Personal VC and FEV values and respiratory status.

Operative options for registration number, temporary and permanent.

The simple test method consists of taking data by means of an electronic spirometer of a single VC (vital capacity) maneuver. By slowly blowing air from a position of maximal inspiration until no more air can be expelled, and an FEV maneuver (forced expiratory volume in the first second) consisting of a forced and continuous exhalation from a position of maximal inspiration, and stopping exhalation after 2.5 seconds (between 2.5 and 3.5 seconds). Following these two maneuvers and having processed by data processing means the results obtained after the expiration in the spirometer microprocessor, the patient's principal parameters and a valuation of the ventilatory function are obtained.

The simple test and the new FEV maneuver are justified and we can even consider it superior to the standard and regular FVC maneuver for obtaining the FEV for the following reasons:

It allows obtaining a FEV correctly. The ATS's (American Thoracic Society) FEV acceptability criteria consists of a satisfactory start of the FVC maneuver and it is obtained before the first second in the curves. Therefore, FEV maneuver can and must comply with these acceptability and reproducibility criteria. Pulmonology societies recommend not discarding FEVs of incomplete FVC maneuvers and they consider that errors at the end of maneuvers do not affect FEVs provided the start is correct.

The spirometric result is obtained from VC and FEV.

The signal taking place between 2.5 and 3.5 seconds that indicates to stop could appear at one second, but it would be too soon to hear it and react; on the other hand, it allows to better evaluate the curves and avoids the tendency to carry out PEF maneuvers consisting of a sudden and quick exhalation as it is done to obtain PEF in peak flow monitors.

Children, adolescents, young people, people with restrictive pathologies and a large number of people without pathologies find it impossible or very difficult to maintain a forced expiration during six seconds.

Unskilled people find it much easier to perform a VC maneuver and a FEV maneuver than a complete forced FVC maneuver.

A prolonged forced expiration (FVC maneuver) in persons with pathologies leads frequently to cough, expectoration, dyspnea, fatigue and/or dizziness which prevent a correct completion of the FVC maneuver. This is not the case with VC maneuver or FEV maneuver.

Several forced and prolonged expirations may cause dizziness, fainting, fatigue and/or discomfort. This is not the case of VC and FEV maneuvers.

A prolonged forced expiration (FVC maneuver) frequently provokes obstruction in asthmatic persons. It rarely happens with a shorter forced expiration (FEV maneuver) or with a slow extended (VC maneuver).

VC and FEV maneuvers are easier to understand and perform by people without prior training than FVC maneuvers. A minimal explanation is sufficient for almost anybody to perform VC and FEV maneuvers.

As a result of the above-mentioned comments, the simple test method can be performed without a technician.

Using the spirometer, object of this patent application, it is possible to perform a complete test consisting of VC maneuvers and FVC (forced vital capacity) maneuvers, as well as the above-mentioned simple test.

Data from the above-mentioned simple test are complemented with measurements of the complete test or normal forced spirometry with all parameters and curves required by presently applicable standard procedures, thus widening the clinical application of spirometry.

The final diagnosis of the pathological process is carried out by a pulmonary function specialist, by using the complete standard test and any studies he may deem convenient. The simple test helps to arrive at this diagnosis and to expand spirometry applications to screening of patients, as well as patient monitoring and proper surveillance.

The method introduces a new FEV maneuver index we call IM, consisting of a two-figure numerical expression based on a flow/time curve that reflects the FEV maneuver performed by the patient/user consisting of a flow/time curve taking time measurement in tenths of a second as the first figure from the maximum flow point to the first second, informing us of the forcefulness of the initial exhalation by the subject; and as the second figure the time in tenths of a second of a descending and concave curve viewed from above, from the maximum flow point until the first second, informing us whether the air exhaled during the first second was strong, continuous and uniform, and that the exhalation during the first second was maintained; the results being then classified with a weighed score from 99 to 00, and appearing on screen after each FEV maneuver (in a simple test) and after each FVC maneuver (in a complete test).

The index allows us to:

Evaluate the maneuver without a curve, since it is not possible for persons unskilled in respiratory functions to evaluate volume/time, flow/time and flow/volume curves. It immediately conveys how the subject has carried out the expiratory effort in an easily comprehensible manner.

Encourage and help subjects improve their maneuvers to try to achieve higher scores.

Store the test data in memory, on paper or on the spirometer screen, as well as monitoring historical data. This helps to see on the monitoring graphs how each FEV maneuver has been carried out, and provides an orientation of the degree of validity.

Know the personal maneuver index (which we will call IMP) corresponding to the personal FEV maneuver index and will be used as a guide to perform a good FEV maneuver, thus customizing the spirometer; that is, each subject has an optimum expiratory effort ("blow") for FEV, which is his own, and this is reflected in the personal maneuver index.

Know the average maneuver index corresponding to the average of all registered indices, and indicate how the patient performs maneuvers, serving as a guide.

Know the average maneuver index for the period under study and provide an orientation of the degree of validity for this period.

In addition to FEV maneuver index and after performing VC, FEV and FVC maneuvers and processing the data, it is possible to visualize on the spirometer screen whether each of the maneuvers performed are acceptable or not in accordance with the ATS's (American Thoracic Society) criteria, as well as the moment in which the test performed meets the ATS's criteria of acceptability and reproducibility by means of a predetermined code or any other visual or audible sign. FEV and FVC acceptability includes volume/time curve uniformity.

The method, object of this invention, includes the possibility of using personal values as reference values, the spirometer performing all the calculations, variability studies and result analysis, using the chosen reference value and also the personal values. Personal values, personal VC and personal FEV are absolute values in VC and FEV liters obtained by a physician when the subject is clinically and functionally stable. These values may be entered manually or directly from the spirometer memory to evaluate the subject's respiratory status.

From the above, it is possible to obtain present values as a percentage of the personal value and the results of VC and FEV variations and variability as a percentage of the reference value and as a percentage of the personal value.

Personal VC and personal FEV are the only two values that provide the actual normal values of a patient without pathology, the values of a stable patient with pathology, and the actual respiratory status or degree of alteration of the patient's stable condition, which cannot be known if only reference value percentages are used. Obstacles and errors found when applying different reference values according to the country of application and the physician or laboratory analyzing the patient, may be avoided by using these personal values. By means of this method and this spirometer it is possible to universalize spirometry and ventilatory function once personal values are known; thus any patients may be analyzed and valued correctly anywhere in the world with the above-mentioned spirometer and method.

The degree of alteration of the present VC and/or FEV in relation to personal VC and FEV is expressed as a coded index representing the respiratory status of a patient; this is the only way of really knowing the subject's ventilatory function alteration and its severity.

The spirometer, object of this patent application, introduces temporary and permanent operative options for registration numbers. It is possible to enter personal data for each patient in the spirometer such as age, weight, height, etc. and use them in the measuring method, and to store with them—temporarily or permanently—data measured and/or the treatment for each of these data entries, storing this information under a personal registration number for each patient.

This registration number contains data, personal values, indices (IM, IMP), variability and values of tests carried out. Its main functions are:

To assure entry of personal data, age, weight, height for each new spirometer user.

To allow the entry of personal VC and personal FEV values.

To allow the personal maneuver indices and the average maneuver indices.

To allow the search of stored data of a same subject.

To allow performing tests with the same device to different subjects at the same time.

To allow these registration number options:

Two temporary options with registration numbers that are manually erased, one with only one registration number for home, workplace, and effort monitoring for patients in a center, and another option with various registration numbers for admitted patients.

Two temporary options with registration numbers that are erased automatically—not manually—at a predetermined time on the following day, allowing the identification of patients up to that time, for emergency services.

Two permanent options of 5 and 10 permanent registration numbers that allow identifying permanently the subject in the device for indefinite self-monitoring, home assistance, and monitoring by a Call Center.

Six permanent options with 20, 50, 100 and more permanent registration numbers that allow identification of subjects permanently in the device, for the purpose of studying, monitoring and following-up patients with periodic visits to doctor's offices, health centers or institutions.

The spirometer, object of this patent application, is turbine of type and, open circuit that does not require calibration (it is factory-calibrated) and only the mouthpiece needs to be replaced between subjects, since the surface containing the turbine is minimal.

In order to transmit data, results and indices obtained, it is possible to use remote transmission means such as a modem associated to the spirometer.

BRIEF DESCRIPTION OF THE DRAWINGS

To facilitate comprehension of the spirometer and method to measure the ventilatory function by spirometry, two figures are attached to this patent application. Their objective is to provide a better understanding of the grounds on which this invention is based and a better understanding of the description of a preferred embodiment; the figures being included for illustration and not for limiting purposes.

DETAILED DESCRIPTION OF THE INVENTION

Figure 1:
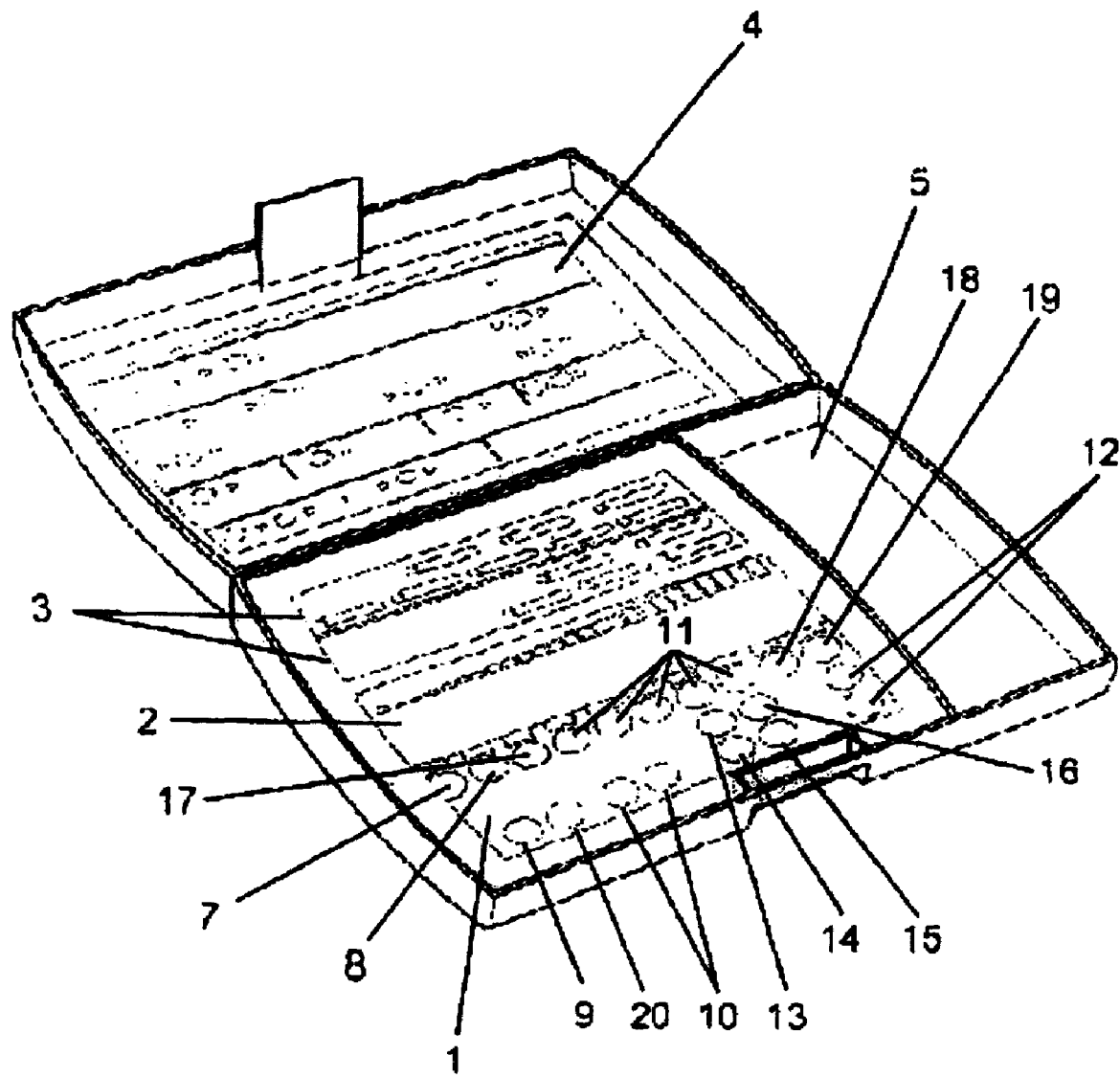
FIG. 1 shows a perspective and working position of the spirometer which is the object of this invention.
Figure 2:
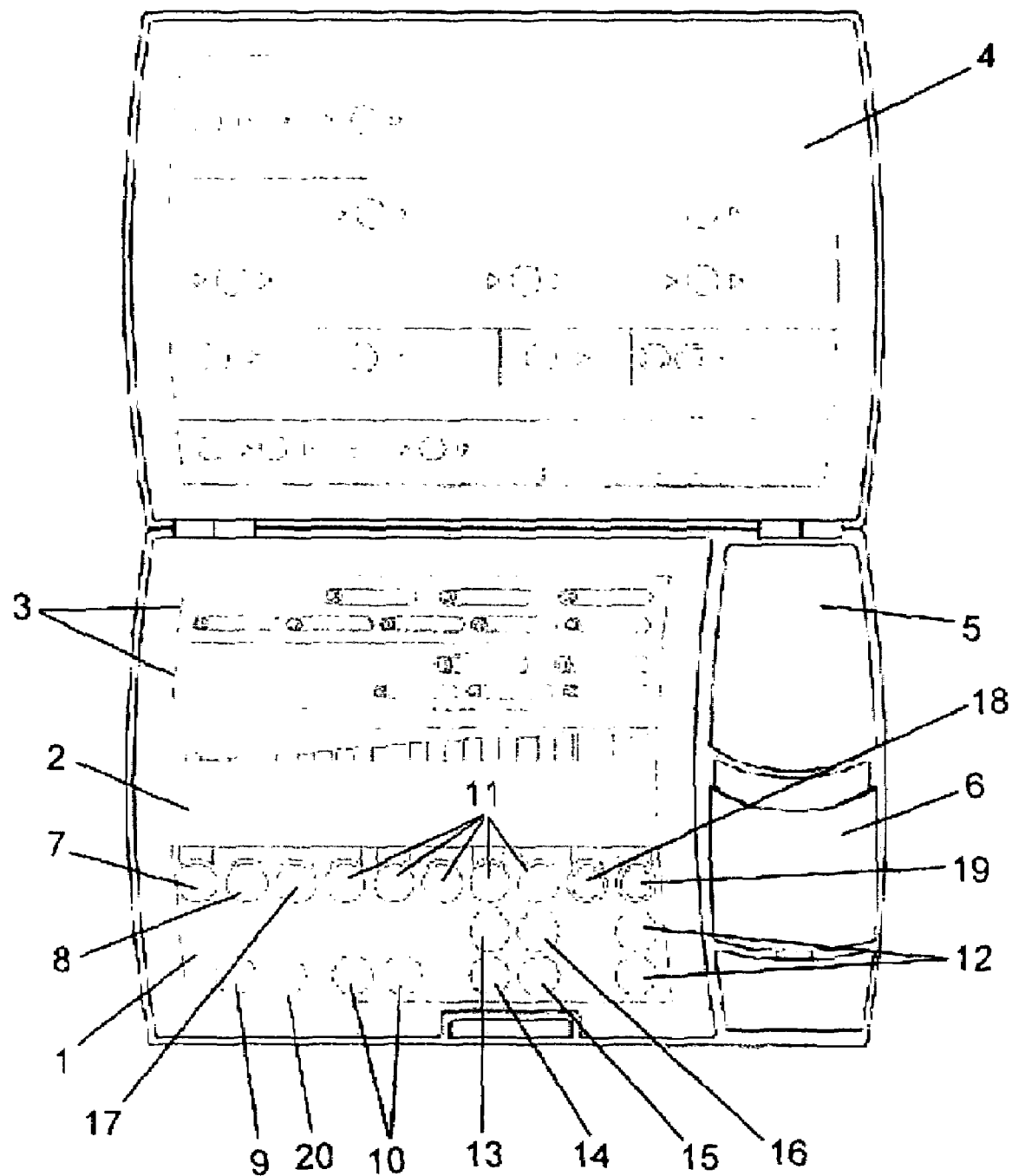
FIG. 2 shows a spirometer plan view with the turbine for air exhalation, in a position prior to storing the spirometer.

As indicated above, the proposed method includes the following steps to measure the ventilatory function by spirometry by means of an electronic spirometer provided with flow detector means, microprocessor control means to carry out calculations on the basis of measured data and means associated to said microprocessor to store the measured results, to visualize the results and to compare the stored results, since it allows carrying out different options in a same device:

Test options—complete test and simple test.

Registration number options—four temporary and eight permanent.

The possibility to set a registration number in each of the above options.

The figures clearly show the keys 1, screen 2, and lighted indicators 3 showing the results and respiratory status, and basic operating instructions 4 for any user that is not skilled in pulmonary functions. The spirometer is enclosed within a folding casing and there is a housing 5 to hold the turbine 6, connected to the spirometer by means of a suitable cable.

When maneuvers are performed screen 2 progressively lights up in function of the percentage of the normal (N) reference value chosen or the personal (P) value, both for VC in the VC maneuver, as well as FEV in FEV maneuver and the FVC maneuver.

During and at the end of the maneuvers, the screen shows:

N or P depending on whether the values indicate the percentage of the normal reference value or personal value. The number underneath N is the reference value chosen (from ATS, European Society, Roca, etc.)

Percentages of VC, FEV or FEV and FVC, depending on the maneuver performed.

NA if the maneuver is not acceptable as per ATS, and A if it is acceptable for VC, FEV and FVC maneuvers.

IM or FEV maneuver index, in FEV maneuver and FVC to evaluate the manner in which the subject has blown.

IMP or personal maneuver index, if it is included in the registration number. It allows comparing the IM performed with IMP.

C when the test complies with ATS's criteria.

At the completion of the test after pressing enter key 13, the following will appear on the screen:

N or P.

VC and FEV as a percentage of the normal or personal reference value.

The percentage of variation with respect to the values of the prior test of the registration number, if there are any, next to VC and FEV. Variation as a percentage of the normal reference value or personal value.

NC if it does not comply with ATS criteria and C if it does.

IMP, if there is one.

IM of the FEV maneuver.

The complete test is performed following the same steps, but pressing FVC key to perform the FVC maneuver.

The device has several registration number options. By pressing option key 7 and the up and down keys 12, we choose the desired option:

Option 001—only one temporary registration number, 1, with a certain number of tests. It is manually erased by pressing option key 7 and registration number key 8 at the same time.

Option 002—several temporary registration numbers with a certain number of tests. It is manually erased by pressing option key 7 and registration number key 8 at the same time.

Options 003 and 004—several temporary 24-hour registration numbers with a certain number of tests; it allows operating from 00:00 hours to 00:00 hours (option 003) and from 12:00 hours to 12:00 hours (option 004) of the following day and they are all erased automatically at that time. It is not possible to erase manually the registration numbers, and the subject is identified until the indicated time.

Options 005 and 010—5 and 10 permanent registration numbers with several tests each; they can never be erased and the subject is forever identified in the device.

Options 020, 050, 100, 250, . . . —consisting of 20, 50, 100, 250, . . . permanent registration numbers, the number of tests being fewer as the number of registrations increases; options may be changed if the number of patients increase, but the registered numbers, their data and basic parameters may never be erased.

The option exists to set a registration number on any option by pressing registration number 8 and enter keys 13 simultaneously; then the registration number together with all personal data appear when starting the device, only allowing basic operations.

The device includes various keys to perform different functions. Option 7 and registration number 8 keys allow:

Changing the registration number.

Entering a registration number immediately following the last one entered.

Changing options by pressing option 7 and enter key 13 simultaneously.

Setting a registration number and going back to the regular option.

Re-starting a test for a patient or initiating a test on another patient.

Entering new normal reference values (from another author).

The number following the last test performed always appears in front of test number key 17, and this digit represents the test number that we are going to initiate.

By pressing simultaneously combinations of key 17 with the print key 14 and enter key 13 allows viewing and printing all desired tests and data with or without curves or with or without graphs.

Personal VC 18 and personal FEV 19 keys allow entering VC and FEV absolute values by pressing simultaneously these keys 18 and 19 and the save key 16. Data from any test performed can similarly be stored in memory; in this case, the FEV maneuver index (IM) is registered as the personal maneuver index (IMP).

These keys also allow viewing values and calculations in screen 2 and printing by choosing between percentages of normal or percentages of personal values, by pressing simultaneously VC personal 18 or FEV personal 19 keys and enter key 13.

This device clearly differentiates keys used to perform a simple test, VC 9 and FEV 20, from the keys to perform a complete test, VC and FVC 10.

A possible method for the use of the spirometer is explained below. The simple test option is comprised of two maneuvers:

Slow VC maneuver: from a maximal inspiration the user blows air slowly until no more air can be exhaled.

FEV maneuver consisting of a strong and continued exhalation from a position of maximal inspiration by blowing air until an audible or visual signal is heard or seen after a minimum preset time that varies between 2.5 and 3.5 seconds, at which time the user may stop the expiration.

To perform these maneuvers, the spirometer must be started by pressing the ON key or option key 7; at this time the screen 2 shows the new registration number as empty, the number of test 1 and the age digits flickering in order to proceed in entering the required data 11, age, height, sex and ethnic group. Numerical digits are entered by means of selection keys 12 that allow a range of values. To obtain a registration number for the new user, save key 16 must be pressed after performing the test and then press enter key 13.

If the user already has a registration number, registration number key 8 must be pressed and the number will be selected by means of selection keys 12; data, the new test number and personal values will then appear and the test may be initiated.

The physician may change the personal values by substituting the old values. The new values will appear in the corresponding registration reference number.

The spirometer allows the initiation of a test by pressing VC 9, not FEV 20, and it includes data regarding age, weight, height, sex, ethnic group, registration number and test number, whether it has personal VC and FEV or not.

To perform any test it is necessary to remove the turbine 6 from its housing 5 in the spirometer, and the turbine 6 remains attached to the spirometer by a cable not shown in these figures. After the turbine has been removed, a disposable mouthpiece is connected to the corresponding turbine end 6.

To perform a simplified test VC key 9 is pressed and after inhaling all air possible and retaining it, introduce the mouthpiece inside the mouth, exhale the air slowly until no more air can be exhaled. The operation is repeated several times by pressing VC key 9 until a higher value is obtained.

FEV 20 key is then pressed, all possible air is inhaled, retained and then the mouthpiece is introduced inside the mouth and the air is exhaled in a strong and continuous manner until a sound is heard at 2.5 seconds. This operation must also be repeated several times as it is also interesting to obtain the highest value and the best FEV maneuver index—IM—.

When the test is completed, enter key 13 is pressed and the most representative values appear on the screen 2. Also, the spirometer indicates whether there is restriction or obstruction and the intensity—light, moderate, intense, severe or very severe—when the corresponding lighted indicators 3 are on. If personal values have been previously entered, the respiratory status will also appear as stable or indicating the degree of alteration.

The complete test is carried out in the same manner but pressing keys 10 and performing the FVC maneuver instead of the FEV maneuver; it is recommended that this test be performed with a physician or a technician trained in pulmonary function.

If a printer is available and it is connected to the spirometer it is possible to print the results by pressing print key 14. All data appearing on the screen will be printed, as well as other additional data and graphs showing the variation for each parameter for each test performed beginning at the number of test indicated. All tests starting from the number of test indicated will be printed.

To transmit results to a personal computer or through a modem, press transmit key 15, in order to later process the data in the computer.

After having performed these maneuvers and checked the FEV maneuver index—IM—and ensured that the simple test complies with ATS's (American Thoracic Society) acceptability and reproducibility criteria, a temporary or permanent registry may be created where a variable number of tests may be stored depending on the number of temporary or permanent registries created. Thus, subjects with respiratory pathologies can be monitored and studied temporarily or permanently in the same device; also allowing to choose the registration number option depending on the desired clinical application.

Data stored in the spirometer may be used in a PC with a suitable software, be checked in the spirometer screen, be printed on a spirometer-associated printer, and be transmitted by remote communication by means of a modem associated to the spirometer.

The spirometer screen will show the FEV maneuver index—IM—and whether the test performed is acceptable or not as per ATS criteria. It will also allow performing the test again, correctly, whenever it is deemed appropriate.

The invention claimed is:

1. Method of measuring the ventilatory function of a patient including obtaining respiratory restriction and obstruction values of a patients by spirometry using an electronic spirometer provided with flow detector means, microprocessor control means to carry out calculations on the basis of measured data, and means associated with said microprocessor to store the measured results, and to visualize the results and compare the stored results, said method comprising the steps of:

capturing data by means of said spirometer of a test consisting of a VC (vital capacity) maneuver, where from a maximal inhalation the subject has to exhale slowly until no more air can be expelled;

capturing data by means of said spirometer of a FEV maneuver consisting of a forced and continuous exhalation from maximal inhalation, and exhaling the air until at least one second has already lapsed;

processing the expiration flow data obtained during the previously-mentioned maneuvers by said microprocessor to obtain main parameters and an evaluation of the ventilatory function and the respiratory condition of the patient; and wherein said data processing step comprises calculating an FEV maneuver index (IM) consisting of a 2-digit numerical expression based on the flow/time curve, which reflects the FEV maneuver performed by the patient, which includes drawing a flow/time curve taking as the first digit of said index the time measurement in tenths of a second, from a maximum flow point until the first second of forced exhalation relative to the initial exhalation intensity of the patient, and as the second digit of said index the time in tenths of a second of descending and concave portions of a curve viewed from above, from the maximum flow point until the first second of forced exhalation, relative to the intensity and the uniformity of the expiration of air during the first second; the results being classified according to a weighted score from 99 to 00.

2. Method, according to claim 1, wherein said minimum predetermined forced exhalation time in said FEV maneuver oscillates between 2.5 and 3.5 seconds.

3. Method, according to claim 1, wherein said forced exhalation time limit is indicated by means of a signal at which time said forced expiration may be stopped.

4. Method, according to claim 1, further comprising the step of capturing by means of said spirometer conventional forced spirometry measurements or complete test with all the parameters and curves required by standard procedures.

5. Method, according to claim 4, further comprising the step of performing an FVC (forced vital capacity) maneuver, wherein said spirometer further comprises a screen, which shows if each VC, FEV and FVC maneuvers performed is acceptable as per a predetermined set of criteria, including uniformity of volume/time curve for FEV and FVC, and wherein said method further comprises indicating the moment in which the test being carried out complies with said predetermined set of criteria as far as acceptability and reproducibility, by means of a preset code or another audible or visual indication.

6. Method, according to claim 1, further comprising the steps of:

inputting into memory personal VC and FEV reference values obtained from an analysis supervised by a physician, when it is deemed that a patient is clinically and functionally stable, and performing a series of variability calculations in relation to said personal VC and FEV reference values from data of subsequent measurements performed by the patient.

7. Method, according to claim 6, wherein said variability calculations with respect to said personal VC and FEV reference values allow expressing the results as a percentage of a normal reference value corresponding to age, weight, height, sex, and ethnicity of the patient and as a percentage of the personal reference value.

8. Method, according to claim 6, wherein present measurement values are prepared by combining them with said personal VC and FEV reference values to provide a result as a percentage of said personal reference values.

9. Method, according to claim 6, wherein the present VC and/or FEV degree of alteration in relation to said personal VC and FEV reference values is expressed as coded index indicating the respiratory status of the subject.

10. Method, according to claim 1, wherein the measured data and/or the result of the processing of each of said data entries is stored in different registration number options, which can be temporary, being erased manually, or temporary, being erased automatically, at a predetermined time, identifying the subject temporarily, and permanent, identifying the subject indefinitely.

11. Method, according to claim 1, further comprising the step of entering personal VC and FEV reference values obtained from an analysis supervised by a physician, when it is deemed that a patient is clinically and functionally stable, and wherein the spirometer provides a personal FEV maneuver index (IMP), which indicates the actual and optimum expiratory effort blow of a subject, and allows comparing said IM performed with said IMP.

12. Method, according to claim 10, wherein an average maneuver index corresponding to the average of all the registration number IM indices, serves as a guide for a period under study and provides an orientation of the degree of validity for said period.

13. Method, according to claim 1, wherein the IM maneuver index is shown on a screen of the spirometer immediately after each FEV maneuver.

14. Method, according to claim 5, wherein the IM maneuver index is shown on said screen of the spirometer immediately after each FVC maneuver.

15. Spirometer comprising:

flow detector means effective to measure Vital Capacity (VC) from a VC maneuver and Forced Expiratory Volume during the first second (FEV) of an FEV maneuver, wherein said flow detection means are of turbine and open circuit type, microprocessor controlled means to carry out calculations from measured data, and means associated with said microprocessor to store the measured results, to visualize the results, and to compare the stored results, said means associated with said microprocessor comprising a plurality of keys for the different test options, for the different registration number options, and for the possibility to set a registration number in each of the above options;

a screen that progressively lights up to indicate function of the percentage of a predetermined normal reference value or a personal reference value obtained from an analysis supervised by a physician, when it is deemed that a patient is clinically and functionally stable, said predetermined normal reference value and said personal reference value are for VC in the VC maneuver, as well as FEV in FEV maneuver and FVC in an FVC maneuver, and a plurality of lighted indicators showing the results and respiratory status, where the indicators indicate whether there is restriction or obstruction and the intensity—light, moderate, intense, severe, or very severe and, if personal values have been previously entered, the respiratory status as stable or indicating the degree of alteration.

16. Spirometer, according to claim 15, wherein the plurality of keys further comprises an option key, a registration number key, up and down keys, a enter key, keys used to perform a simple test (VC, FEV), keys to perform a complete test (VC, FVC), a test number key, a print key, a transmit key, a save key, a VC personal key, a FEV personal key and a plurality of keys for entering the required data of age, height, sex and ethnic group.

17. Spirometer, according to claim 15, wherein said spirometer is associated with means for remote transmission of results.

18. A method for measuring ventilatory function and specifically for obtaining respiratory restriction and obstruction values of a patient comprising the steps of:
  using an electronic spirometer having flow detector means, microprocessor control means to carry out calculations on the basis of measured data, and means associated with said microprocessor for storing the measured results, for visualizing the results, and for comparing the stored results;
  data entry by means of said spirometer, said data being obtained by a first test comprising a VC (vital capacity) maneuver, where from a maximal inspiration said patient exhales slowly until no more air can be expelled; and by a second test comprising a FEV maneuver (forced expiratory volume during the first second) consisting of a forced and continuous exhalation from maximal inspiration, and exhaling the air until a minimum predetermined time has elapsed;
  processing, by computer means, the expiration flow data obtained during said VC and FEV maneuvers;
  wherein said procession step comprises calculating an FEV maneuver index (IM) consisting of a 2-digit numerical expression based on the flow/time curve, which reflects the FEV maneuver performed by the patient, which includes drawing a flow/time curve taking as the first digit of said index the time measurement in tenths of a second, from a maximum flow point until the first second of forced exhalation relative to the initial exhalation intensity of the patient, and as the second digit of said index the time in tenths of a second of descending and concave portions of a curve viewed from above, from the maximum flow point until the first second of forced exhalation, relative to the intensity and the uniformity of the expiration of air during the first second; the results being classified according to a weighted score from 99 to 00;

and obtaining the main parameters and an evaluation of the ventilatory function and the respiratory condition of the patient.

* * * * *